US009846117B2

United States Patent
Zhou et al.

(10) Patent No.: US 9,846,117 B2
(45) Date of Patent: Dec. 19, 2017

(54) OPTICAL ABSORBANCE MEASUREMENTS WITH SELF-CALIBRATION AND EXTENDED DYNAMIC RANGE

(75) Inventors: Xin Zhou, Beijing (CN); Xiang Liu, Phoenix, AZ (US); Alfred Feitisch, Los Gatos, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 681 days.

(21) Appl. No.: 12/814,315

(22) Filed: Jun. 11, 2010

(65) Prior Publication Data
US 2011/0032516 A1     Feb. 10, 2011

Related U.S. Application Data

(60) Provisional application No. 61/186,749, filed on Jun. 12, 2009.

(51) Int. Cl.
| | |
|---|---|
| *G01J 3/433* | (2006.01) |
| *G01N 21/39* | (2006.01) |
| *G01N 21/03* | (2006.01) |
| *G01N 21/05* | (2006.01) |
| *G01N 21/3504* | (2014.01) |
| *G01N 21/27* | (2006.01) |

(52) U.S. Cl.
CPC ............ *G01N 21/39* (2013.01); *G01J 3/4338* (2013.01); *G01J 3/433* (2013.01); *G01J 2003/4332* (2013.01); *G01J 2003/4334* (2013.01); *G01N 21/031* (2013.01); *G01N 21/05* (2013.01); *G01N 21/274* (2013.01); *G01N 21/3504* (2013.01); *G01N 2021/354* (2013.01); *G01N 2021/399* (2013.01)

(58) Field of Classification Search
None
See application file for complete search history.

(56) References Cited

U.S. PATENT DOCUMENTS

| | | | |
|---|---|---|---|
| 5,173,749 A | 12/1992 | Tell et al. | |
| 6,356,350 B1 * | 3/2002 | Silver et al. | 356/437 |

(Continued)

FOREIGN PATENT DOCUMENTS

| | | |
|---|---|---|
| EP | 1850116 | 10/2007 |
| JP | 2007-298510 A | 11/2007 |

(Continued)

OTHER PUBLICATIONS

Miles J. Weida, Daylight Solutions, 2007, pp. 1-5, D0084, Rev. A.*
D'Amato, F. et al. "Realization of a Methane leaks detector for roads inspection." *Lasers and Electro-Optics Europe 2003. Cleo/Europe.* 2003 Conference. Munich, Germany. Jun. 22-27, 2003. IEEE. (2003):494.

(Continued)

*Primary Examiner* — Neil N Turk
(74) *Attorney, Agent, or Firm* — Mintz Levin Cohn Ferris Glovsky and Popeo, P.C.

(57) ABSTRACT

Detector data representative of an intensity of light that impinges on a detector after being emitted from a light source and passing through a gas over a path length can be analyzed using a first analysis method to obtain a first calculation of an analyte concentration in the volume of gas and a second analysis method to obtain a second calculation of the analyte concentration. The second calculation can be promoted as the analyte concentration upon determining that the analyte concentration is out of a first target range for the first analysis method.

19 Claims, 4 Drawing Sheets

(56) References Cited

U.S. PATENT DOCUMENTS

| | | | |
|---|---|---|---|
| 6,868,285 B2 | 3/2005 | Muller-Dethlefs | |
| 7,616,316 B1 | 11/2009 | Silver et al. | |
| 2003/0111607 A1 | 6/2003 | Bachur et al. | |
| 2003/0176777 A1 | 9/2003 | Muller- Dethlefs | |
| 2005/0046852 A1* | 3/2005 | Larking | G01J 3/433 356/437 |
| 2006/0262311 A1* | 11/2006 | Muta | G01J 3/433 356/437 |

FOREIGN PATENT DOCUMENTS

| | | |
|---|---|---|
| WO | WO-93-15391 A1 | 8/1993 |
| WO | WO-2007120931 A1 | 10/2007 |

OTHER PUBLICATIONS

Wang, Liang-Guo. "A H20(v) Sensor System for Combustion Diagnostics Using Both Direct Absorption and Frequency Modulation Spectroscopy." *LEOS '95. IEEE Lasers and Electro-Optics Society 1995 Annual Meeting. 8th Annual Meeting. Conference Proceedings.* Oct. 30-31, 1995; San Francisco, CA. USA. IEEE. New York, NY. USA. vol. 2. (Oct. 30, 1995):329-333.

Zondlo, M. et al. "Development of a lightweight, fast and accurate hygrometer for use on balloons and aircraft." *SPARC 2004. 3rd General Assembly of the WCRP Project.* SPARC. Stratospheric Processes and their Role in Climate, Programme and Abstracts. Aug. 1, 2006:242. [retrieved on Apr. 25, 2014].

* cited by examiner

OPTICAL ABSORBANCE MEASUREMENTS WITH SELF-CALIBRATION AND EXTENDED DYNAMIC RANGE

CROSS-REFERENCE TO RELATED APPLICATIONS

This application claims the benefit of U.S. provisional patent application Ser. No. 61/186,749, filed on Jun. 12, 2009 and entitled "Online Self-Calibrating Optical Absorption Sensors with Expanded Dynamic Range" which is incorporated by reference herein in its entirety.

TECHNICAL FIELD

The subject matter described herein relates generally to optical absorbance measurements, and in more specific implementations to providing self-calibration capabilities and extended dynamic measurement ranges to optical absorbance sensors.

BACKGROUND

Various spectroscopic techniques have been and continue to be demonstrated for trace gas detection using a wide variety of light sources. Two absorbance spectroscopy techniques available for such measurements are direct absorbance spectroscopy and modulation spectroscopy. Though somewhat different in principle, these two techniques both can be used to measure important parameters such as temperature, pressure, gas velocity and species concentration in practical environments. However, each of these techniques includes limitations that can render it less desirable for providing optimal measurement accuracy and/or precision over a wide dynamic range.

SUMMARY

In one aspect, a method includes receiving, at a processor, detector data representative of an absorbance of light emitted from a light source as the light passes through a volume of gas over a path length. The volume of gas comprising an analyte at an analyte concentration. The detector data are analyzed using a first analysis method to obtain a first calculation of the analyte concentration and using a second analysis method to obtain a second calculation of the analyte concentration. The first analysis method has a first target and the second analysis method has a second target range that differs from and extends outside of the first target range. If the first calculation of the analyte concentration indicates that the analyte concentration is outside of the first target range, the second calculation is promoted as the analyte concentration.

In optional variations, one or more of the following features can be included. The first analysis method can include modulation spectroscopy and the second analysis method can include direct absorbance spectroscopy. The first target range can include values of the analyte concentration between zero and a threshold analyte concentration. The threshold analyte concentration can be predetermined based on analysis of one or more calibration samples using the first analysis method. The light source can include a tunable laser source emitting light in range of wavelengths. The detector data can include intensity data for the light emitted from the light source both with and without a modulation frequency.

The first analysis method can include modulation spectroscopy using a first absorbance transition for the analyte and the second analysis method can include modulation spectroscopy using a second absorbance transition for the analyte. The first absorbance transition can be stronger than the second absorbance transition. The second analysis method can include direct absorption spectroscopy using a first absorbance transition for the analyte and the second analysis method can include modulation spectroscopy using a second absorbance transition for the analyte. The first absorbance transition can be stronger than the second absorbance transition. The first absorbance transition for the analyte and the second absorbance transition for the analyte can both be within a scan range of a tunable laser. The light source can include a first tunable laser with a first scan range that can include the first absorbance transition for the analyte and a second tunable laser with a second scan range that can include the second absorbance transition for the analyte. With the analyte concentration in a calibration range in which a first effective range of the first analysis method and a second effective range of the second analysis method overlap, the second calculation of the analyte concentration can be used to calibrate the first analysis method.

The light source can include one or more of a tunable diode laser (TDL), a quantum cascade laser (QCL), a horizontal cavity laser, a vertical cavity surface emitting semiconductor laser (VCSEL), and a device for nonlinear frequency generation of tunable light. A detector device can be used to provide the detector data and can include one or more of a photodiode, a photodetector, and a photoacoustic detector. A sample cell can contain the volume of gas for passage of the light between the light source and a detector that quantifies the absorbance.

In an interrelated aspect, a method can include receiving detector data representative of absorbances of light emitted from a light source as the light passes through a volume of gas over a path length. The volume of gas includes an analyte at an analyte concentration and a background compound at a background compound concentration. The absorbances include a target absorbance influenced by the analyte concentration and the background gas concentration and a reference absorbance influenced by the background gas concentration. The detector data are analyzed using a direct absorbance method to obtain a first metric representative of the reference absorbance. The detector data are also analyzed using a modulation spectroscopy method to obtain a second metric representative of the target absorbance. The second metric is adjusted using the first metric to estimate a contribution to the second metric due to the analyte concentration. The analyte concentration is determined based on the contribution to the second metric due to the analyte concentration, and the analyte concentration is promoted.

Optionally, the light source can include a modulated tunable laser having a first scan range that includes at least part of the target absorbance and an unmodulated tunable laser having a second scan range that includes at least part of the reference absorbance.

Articles are also described that comprise a tangibly embodied machine-readable medium operable to cause one or more machines (e.g., computers, etc.) to result in operations described herein. Similarly, systems are also described that may include a processor and a memory coupled to the processor. The memory may include one or more programs that cause the processor to perform one or more of the operations described herein.

The presently disclosed subject matter may provide one or more benefits, including but not limited to extending the dynamic range of a gas analyzer, enabling self-calibration functions, and providing improved approaches for calibration in corrosive environments. Analyzers implementing one or more aspects of the presently disclosed subject matter can measure a wide range of target species from ppm level to percent level, can be used for different background gases without the need for recalibration, and can eliminate the difficulties associated with calibration in corrosive gases/environments.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
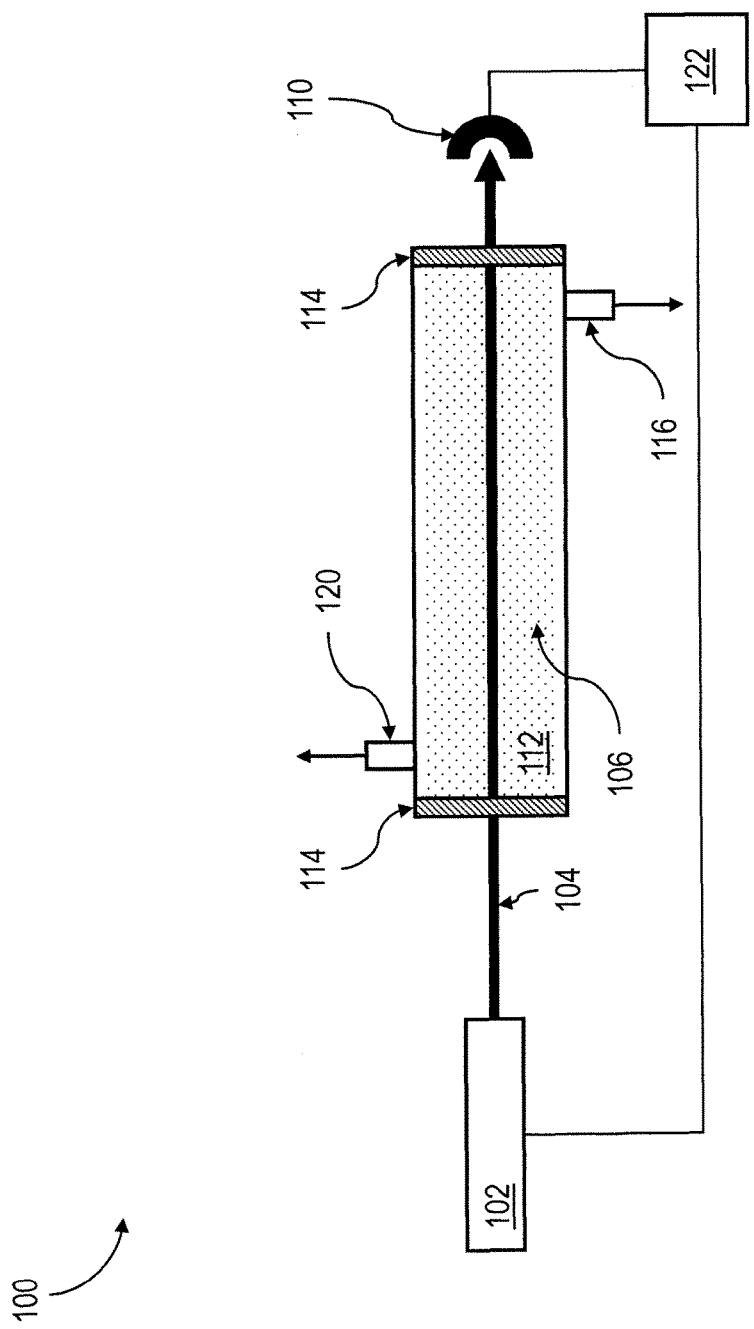
FIG. 1 is a schematic diagram illustrating a spectroscopic measurement system.

As shown in FIG. 1, a system 100 can include a light source 102 operating at the target wavelength that provides a continuous beam or pulses of light 104 that pass through a volume 106 of a sample gas before being detected by a detector 110. The light source 102 can include one or more lasers, for example a tunable diode laser (TDL), a quantum cascade laser (QCL), a horizontal cavity laser, a vertical cavity surface emitting semiconductor laser (VCSEL), or other similar devices for nonlinear frequency generation of tunable light. The detector 110 can include one or more of a photodiode, photodetector, or photoacoustic detector. In some implementations, the volume 106 of the sample gas can be contained in a sample cell 112 having one or more windows 114 through which the continuous beam or pulses of light 104 pass into and out of the volume 106. The sample cell 112 can be a flow through cell as shown in FIG. 1, in which gas flows into the sample cell 112 via an inlet 116 and out of the sample cell 112 through an outlet 120. Other configurations are possible besides that shown in FIG. 1. For example, a path length of the continuous beam or pulses of light 104, which is the distance the continuous beam or pulses of light 104 travels through the sample gas 106 can be established using mirrors, beam splitters, or by varying other geometrical parameters such as the location of the light source 102 and/or the detector 110. Depending on the analyte or analytes to be measured, the concentration range over which the analyte or analytes are expected to be present, and the presence of other compounds or materials that might interfere with the accuracy of a measurement in the sample gas 106, the continuous beam or pulses of light 104 can be projected through free gas (such as for example in a pipeline) or even free air. Alternatively, a batch volume of sample gas 106 can be analyzed in a sample cell, for example one such as that shown in FIG. 1 with additional valving and/or vacuum or pumping means to deliver a first batch volume of the sample gas 106 and remove that first batch volume from the sample cell 110 to prepare for analysis of a second batch volume.

Modulation spectroscopy is a widely used technique for sensitive trace-species detection. In modulation spectroscopy, the wavelength (or, alternatively, the amplitude) of the light source 102 is modulated at a modulation frequency f and light emitted by the laser light source 102 is passed through the sample gas 106 over a path length. The intensity of the continuous beam or pulses of light 104 as it impinges on the detector 110 varies in amplitude. Fourier analysis of the signal generated by the detector 110 includes signal components at the modulation frequency f as well as at harmonic frequencies at multiples of the modulation frequency f (2f, 3f, 4f, etc.). Demodulation of one of the harmonic frequencies, for example the 2f, yields a signal that can be used to very accurately determine the frequency of one or more analytes in the sample gas 106. By shifting phase-sensitive detection to higher frequencies, modulation spectroscopy can significantly reduce 1/f noise and achieve high sensitivity. In some examples, the height of a single absorbance line characteristic of the analyte can be quantified as representative of the analyte concentration in the sample gas 106. Modulation spectroscopy can be highly sensitive for detecting and quantifying low analyte concentrations, and an analyte concentration can be quantified directly from the demodulated signal from the detector. Additionally, a lock-in amplifier or other signal filtering processes or devices can be used to isolate absorbance signals due to the analyte from background drift or other noise in the instrument.

However, many hardware-related parameters including the laser intensity, detector gain setting, signal amplification, lock-in amplifier settings, and the like may affect the magnitude and the shape of the 2f signal. As such, sensors based on modulation spectroscopy can require calibration at a reference condition to eliminate the dependence of hardware-related parameters. Hardware-settings typically can not be changed once the calibration is done. Trace gas analyzers based upon 2f-spectroscopy may also be limited in their dynamic range. The measurement range may be limited for a number of reasons, including, but not limited to the limited resolution of data acquisition devices and the limited linear response of the 2f signal to trace gas concentration.

Another potential issue in modulation spectroscopy analyzers can arise due to the sensitivity of the harmonic lineshape to changes in background gas composition. Different gases in the background stream can have different impacts on the harmonic lineshape. The harmonic lineshape directly determines the accuracy of the trace gas measurement, with reference to the analyzer's calibration. The change in lineshape due to interaction of the measured trace gas with other gases in the complete stream is referred to as collisional broadening. For example, a 2f-based analyzer calibrated for measuring moisture in pure $N_2$ can need to be returned to the manufacturer for recalibration if the customer wishes to instead measure moisture in pure $O_2$, air or $CO_2$. The different mass of the background molecules and the structure of the molecules can result in profound impact on the 2f lineshape and thus the concentration reading. As an example, a 2f harmonic spectroscopy tunable diode laser (TDL) analyzer calibrated for moisture in $N_2$ has been demonstrated to require multiplication of the concentration reading by a factor of 1.25/2.25/0.38 when changing the background gas from $N_2$ to air/$O_2$/$CO_2$, respectively, at a selected frequency modulation amplitude, while keeping the moisture concentration constant. Calibration of modulation spectroscopy-based analyzers can therefore require a representative stream that contains all components that may occur in the stream for which the analyzer is to be operated. Providing a representative stream can in some instances be difficult, costly or dangerous to human health for corrosive gas streams, such as for example for moisture in pure ammonia, in pure chlorine or in pure HCl, for gas streams containing toxic gases such as high concentrations of $H_2S$ or $ASH_3$, $PH_3$ HCN and the like. Calibration for such analytical conditions should be done with great care and can require extensive safety precautions and a costly safety infrastructure for operating toxic and highly corrosive gases.

Nonetheless, trace measurements of moisture, $CO_2$, $H_2S$ $C_2H_2$ and other contaminants are critically important in optimizing and safe guarding petrochemical production and natural gas gathering, processing and transport. Modulation spectroscopy can be used to provide the desired levels of accuracy at normal process operating conditions. However, upset conditions, such as for example a moisture plug in a pipeline, a reactor cleaning event, or other factors that might cause the concentration of a target analyte to increase temporarily by one, two, or even more orders of magnitude can cause an instrument having a relatively narrow dynamic range to experience an out of range error. Even if an instrument using a modulation spectroscopy method were tuned to allow a broader dynamic range, non-linearity of the harmonic signal can arise as the concentration increases.

In direct absorbance spectroscopy, the wavelength of the light source 102 need not be modulated. The intensity of the continuous beam or pulses of light 104 as it impinges on the detector 110 is quantified as a function of wavelength. Typically, an absorbance spectrum is analyzed to determine the area under the curve of an absorbance peak of one or more analytes. Once the entire line shape can be well resolved, the integrated area under the isolated line shape is independent of line broadening effects. This makes direct absorbance techniques very robust in hostile environments where rapidly varying gas composition and pressure change the lineshape due to collisional broadening effects. Additionally, the spectrally resolved line shapes may be used to distinguish the contributing absorbances from nearby transitions of background species. Direct absorbance can also determine the absolute species concentration without any calibration, once the total pressure, pathlength and linestrength are known. Direct absorbance can be effective over a much broader range of analyte concentrations than can a harmonic absorbance measurement.

However, direct absorbance techniques may also suffer from various disadvantages. The baseline fit can become difficult when the line is broadened and blended with neighboring lines from the analyte itself and/or background species. Direct absorbance generally has relatively low detection sensitivity because of the direct addition of noises. This shortcoming can limit the use of direct absorbance methods for trace gas sensing in the field. Additionally, correction for a non-zero baseline that can vary due to scattering, refraction, or absorbance due to particles or other gases in sample gas 106 can be required as well. Additionally, a lock-in amplifier cannot readily be used to isolate the analyte absorbance signal from electronic or background noise from the measurement system, optics, sample gas, etc. The correction can be obtained using measurements of calibration gas of a known concentration. Aging effects can also be important in direct absorbance spectroscopy, as system and background noise may vary over time. In previously available systems, periodic recalibration can be required for accurate analysis over a prolonged service period.

Thus, while the use of modulation spectroscopy can be advantageous at low analyte concentrations where very low absolute uncertainty is desirable, over a large dynamic concentration range, substantial inaccuracy can be introduced. Conversely, while direct absorbance spectroscopy can provide a broad dynamic range, reduced relative accuracy is available at lower concentrations.

Implementations of the currently disclosed subject matter can include systems, methods, apparatuses, and devices that provide self-calibration capabilities and extended dynamic ranges for optical absorbance measurements of chemical analytes. Calibration difficulties, for example those that can be associated with toxic and corrosive gases, can also be overcome. Direct absorbance techniques can be used in combination with modulation spectroscopy. In some implementations, a detection scheme can be switched between a direct absorbance measurement technique and a modulation spectroscopy measurement technique, in some implementations using the same light source, detector, and other optical equipment. By combining direct absorbance techniques and modulation spectroscopy, one or more problems inherent in modulation spectroscopy can be overcome, potentially including but not limited to limited dynamic range, labor-intensive calibration procedures, and limited tolerance to background stream variations, as can one or more problems inherent in direct absorbance techniques, potentially including but not limited to reduced detection sensitivity (relative to modulation spectroscopy), and baseline ambiguity.

Figure 2:
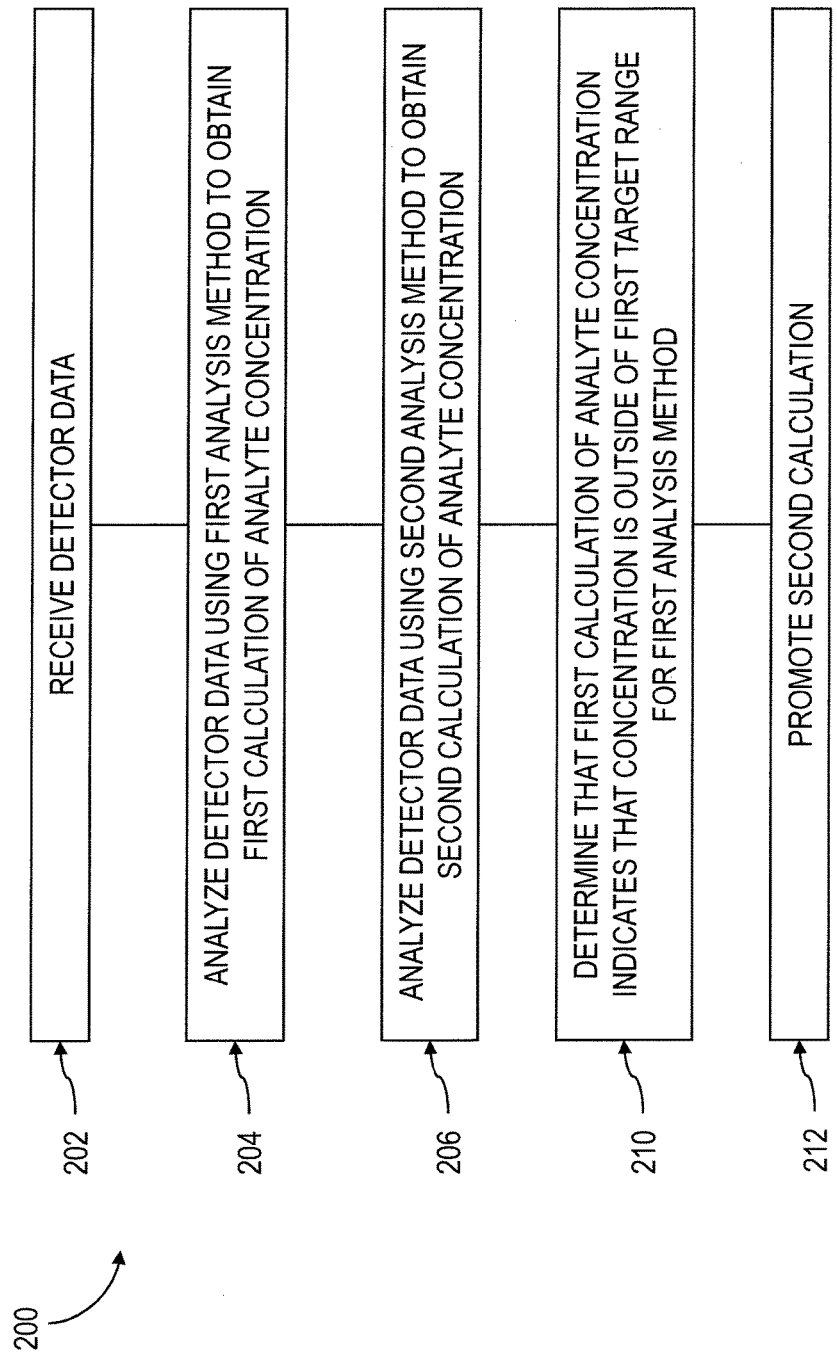
FIG. 2 is a process flow diagram illustrating a method.

A method consistent with the current subject matter is illustrated in the process flow chart 200 of FIG. 2. At 202, detector data are received, for example at a processor. The detector data are representative of an absorbance of light emitted from a light source as the light passes through a volume of gas over a pathlength. The volume of gas includes an analyte at an analyte concentration. The analyte concentration can absorb some of the intensity of the light passing through the gas over the pathlength. At 204 and 206, respectively, the detector data are analyzed using a first analysis method and a second analysis method to obtain a first calculation and a second calculation of the analyte concentration. If, at 210 the first calculation of the analyte concentration is determined to indicate that the concentration is outside of a first target range for the first analysis method, at 212 the second calculation is promoted as the analyte concentration. The promoting can include storing the second calculation to a computer-readable medium, displaying the second calculation on a display device or printout, or the like.

In some implementations, the light source 102 can be a tunable laser. The first analysis method can be modulation spectroscopy and the second analysis method can be direct absorbance spectroscopy, which can both be executed using the same light source 102 and detector 110. A controller 122 as shown in FIG. 1 can be incorporated to receive and analyze the detector data from the detector 110 and to control the light source 102 according to the analysis method to be used. The detector data can be provided from a detector that can include one or more of a photodiode, a photodetector, and a photoacoustic detector.

In one or more implementations, a laser drive circuit can be programmed to turn on/off the high frequency modulation on the laser scan of a tunable diode laser. When the species concentration inferred from the measured harmonic modulation signal is larger than a pre-set value which is calculated to insure the corresponding absorbance is greater than a threshold, such as for example 0.1, the program can cut off the high frequency modulation and the measurement technique can thereby switch from harmonic absorbance to direct absorbance. The species concentration can then be determined by the integrated area of the absorbance lineshape using the known total pressure, pathlength and linestrength.

Because a direct absorbance technique can obtain absolute species concentrations from the integrated area of the lineshape, it can be used to calibrate the modulation spectroscopy signal. In one implementation, this self-calibration may be done as follows. A gas mixture containing a target species with a species concentration within a certain pre-set range so that the resultant absorbance is between, for example, 0.01 and 0.1, is passed through the analyzer. A calibration sequence can be initiated, for example by a user pressing a "calibration" button on the analyzer, causing a software program to automatically make measurements using both modulation spectroscopy and direct absorbance techniques. As an example, a modulation spectroscopy signal can be measured for 1 min before the system is switched to a direct absorbance technique for another 1 min. The measured concentration from the direct absorbance technique can be used to calibrate the previously measured modulation spectroscopy signal. By changing the operating pressure, a pressure correction calibration may be completed in the same way.

Figure 3:
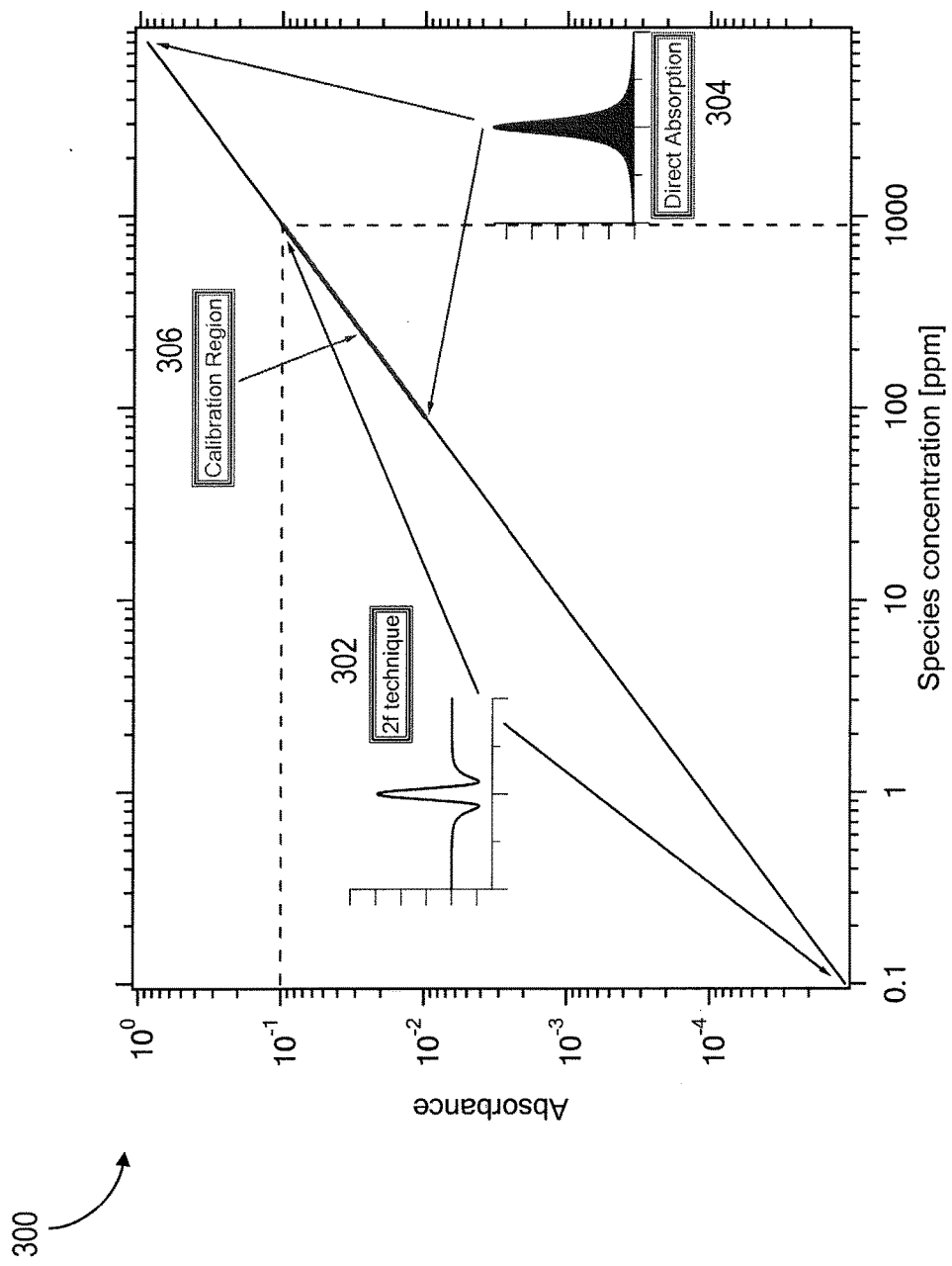
FIG. 3 is a chart illustrating aspects of the method in FIG. 2.

FIG. 3 shows a chart 300 illustrating details of a measurement strategy according to the presently disclosed subject matter and including extended dynamic range and "self-calibration" functions, which are described in greater detail below. The example shown in FIG. 3 is based on one specific absorbance transition and path length. In this case, an absorbance of $10^{-4}$ corresponds to a species concentration of 0.9 ppm. Based on the measurement strategy disclosed herein, when absorbance is greater than $10^{-2}$ (90 ppm in this case), the program can automatically switch from a 2f harmonic (modulation) spectroscopy analysis method 302 to direct absorbance 304. To avoid possible optically dense problems, the measurement range may be limited to absorbances of less than approximately 0.8 (which corresponds to a concentration of about 7200 ppm in this case). In this manner, the analyzer may have a much extended measurement range relative to a typical 2f analyzer. In the example discussed here, the measurement range may be extended from 0~90 ppm to 0~7200 ppm.

In another implementation consistent with the current subject matter, dynamic range limitations can be addressed by using two absorbance transitions (one stronger absorbance transition and one weaker absorbance transition) which occur at nearby wavelengths. In this instance, the first and the second analysis methods can both be the same (for example, modulation spectroscopy). The analyzer can employ the stronger absorbance transition for a low measurement range, and use the weaker absorbance transition for the high measurement range, thereby extending the measurement range compared with only using a single absorbance transition.

In some variations, two appropriate absorbance transitions which are close enough to be scanned by a single tunable laser light source can be used. Depending on the analyte and background composition of the sample gas 106, it might be difficult to find two absorbance transitions which have a necessary frequency separation. If the two absorbance transitions are too close each other, the two lines can overlap and the wing of the strong transition can influence the measurement of the weaker absorbance transition. The measurement accuracy can thereby be impaired. If the two absorbance transitions are not close enough to be covered by a single laser scan, the operating temperature of a diode laser providing incident light can be changed manually or via a programmed procedure to reach each absorbance transition. This can increase the operating difficulties and reduces the robustness of the analyzer. It is also not always practical to find the appropriate absorbance line pairs, especially when considering interferences from background gases. A second tunable laser in the light source can be incorporated into the light source 102 to cover the second absorbance transition.

Pre-calibration can be used to address the issue of recalibration for different background gases. In this approach, pre-calibrations of an instrument for different background gases can be prepared and pre-programmed into an analyzer in advance based on expected background gases. For example, if a customer plans to measure moisture concentrations in either $N_2$ or $H_2$, an analyzer may be calibrated on both $N_2$ and $H_2$ background in the factory. Different calibration coefficients are recorded and stored in the analyzer. A user would then select the corresponding calibration coefficients based on the background gas being analyzed. One potential drawback to this approach is that analysis of a background gas for which the instrument is not pre-calibrated requires a new calibration. In addition, this approach does not address dynamic range issues or problems with corrosive gases. Furthermore there is no known method to enable the analyzer to automatically choose between two stored background gas calibrations when both background gases have no absorbance in the spectral range where the trace analyte is being measured. Such an automated approach can be advantageous for situations in which switching between a measurement stream containing infra red absorbing gases such as hydrocarbon gases and gases such as $N_2$, air, $O_2$, $H_2$, $Cl_2$ or noble gases that have no absorbance at the particular wavelength being used for measuring the trace analyte, under actual operating conditions.

If the background gases in a gas mixture to be analyzed are highly corrosive, calibration should be done with great care. To prevent corrosion from background gases, the whole calibration system should be made of high corrosion resistance materials. This can generally increase the analyzer cost, and can require additional labor for system configuration. Finding a good approach for preparing such a calibration can also be quite difficult. For example, to calibrate an analyzer to determine moisture concentrations in pure ammonia or chlorine or other active gases, a chilled mirror cannot be used as reference for the moisture concentration, because the active component will react with the moisture dew deposit, causing erroneous "acid" dew point readings. Permeation tubes are another possible calibration approach. Permeation tubes generally work best for trace level ranges and require very precise temperature and flow rate control of the carrier gas. It is not easy to generate percent level moisture in corrosive gases.

In a further extension of the current subject matter, an overlap region 306 between the first analysis method and the second analysis method can be used for "self calibration" of the instrument. By switching measurement schemes between modulation spectroscopy and direct absorbance for a gas having an analyte concentration in the overlap region 306, the peak height of a modulation spectroscopy signal can be calibrated by the integrated area of direct absorbance. In this manner, analysis of a gas mixture with different background gases that what an analyzer is preset for can be possible without factory recalibration. Instead, the analyzer can be self-calibrated. The gas used for this self-calibration procedure can be either a calibration gas with a known concentration or, alternatively, the sample gas.

The combination of direct absorbance and modulation spectroscopy methods in a single instrument can further provide a valuable internal self-check capability to monitor instrument performance over time. In some implementations, data collected for measurements in the overlap region 306 can be logged and compared with initial performance of the instrument when it is in pristine condition with a factory calibration. An offset between the two measurements in the overlap region 306 is likely to be present, even at initial conditions. However, observations of how this offset changes can be used to self-correct for changes in the instrument response to a given analyte concentration, for example due to buildup of contamination on optical surfaces due to aging, condensation, etc. Deviations in the offset can be detected and an algorithm constructed to provide ongoing self-correction.

The above-described approach to instrument self-correction can be advantageous because modulation spectroscopy is generally unaffected by factors that affect the base spectral response—these factors do not appear in the higher order harmonic signals—but can be affected by DC attenuation effects and collisional broadening induced errors in the harmonic signal. In contrast, direct absorbance directly measures the spectral lineshape of the absorbance response and therefore shows effects of collisional broadening, optical contamination, and the like.

Using the current subject matter, it is possible to compensate for collisional broadening effects on the harmonic lineshape using direct absorbance. The harmonic lineshape can in some instances be considered as analogous to the second derivative of an absorbance peak. As such, the peak to valley height, which is typically the measured parameter in modulation spectroscopy, can depend critically on the lineshape of peak. In contrast, direct absorbance makes use of the integrated area under the lineshape and is thus a more direct measurement of an analyte concentration that does not require assumptions about the shape of the peak.

Thus, using a direct absorbance measurement and a modulation spectroscopy measurement of a gas sample, it a scaling factor to relate observed peak heights in the harmonic method to actual concentrations can be estimated. Such measurements can be made when the process conditions provide a concentration in the overlap region 306, or alternatively, by periodically injecting a reference gas with a known concentration in the overlap region 306 or containing sufficient concentration of analyte to raise the process condition concentrations temporarily into the overlap region 306.

According to a further implementation of the current subject matter, a modulation spectroscopy method can be used to analyze a target absorbance transition of an analyte in a gas sample. A direct absorbance method can be used concurrently or sequentially with the modulation spectroscopy method to analyze a reference absorbance transition that is characteristic of a background compound present in the gas sample. In addition to the reference absorbance transition, the background compound can also have an interfering background absorbance transition that overlaps with or otherwise confounds accurate characterization of the target absorbance transition using the modulation spectroscopy method. A concentration of the background compound in the gas sample can be inferred based on the reference absorbance transition analyzed by the direct absorbance method. Using this inferred concentration of the background compound, a calculation can be made regarding how much of the spectral response observed with the modulation spectroscopy method at the target absorbance transition is due to the effects of the interfering background absorbance transition. A background gas adjustment factor can be determined to relate the quantified absorbance at the reference absorbance transition to light absorbance quantified at the target absorbance transition that is due to the background compound. Using the background gas adjustment factor, the concentration of the analyte in gas sample can be calculated by adjusting the absorbance observed at the target absorbance transition using an inferred amount of interference by the background compound at the target absorbance transition.

Use of the direct absorbance method to characterize the reference absorbance transition can be important in gas samples having a very large background concentration of one or more compounds that have spectral transitions that might overlap with the target absorbance transition of the analyte. For example, in a natural gas or methane background, use of a modulation spectroscopy method to quantify the reference absorbance transition can limit the number of peaks of the absorbance spectrum of the background compound if the background compound is present at very high concentrations. In such a situation, a modulation spectroscopy method may be useful only for absorbance transitions of the background compound that have very weak absorbance because of the relatively narrow dynamic concentration range over which modulation spectroscopy can be accurately applied.

Figure 4:
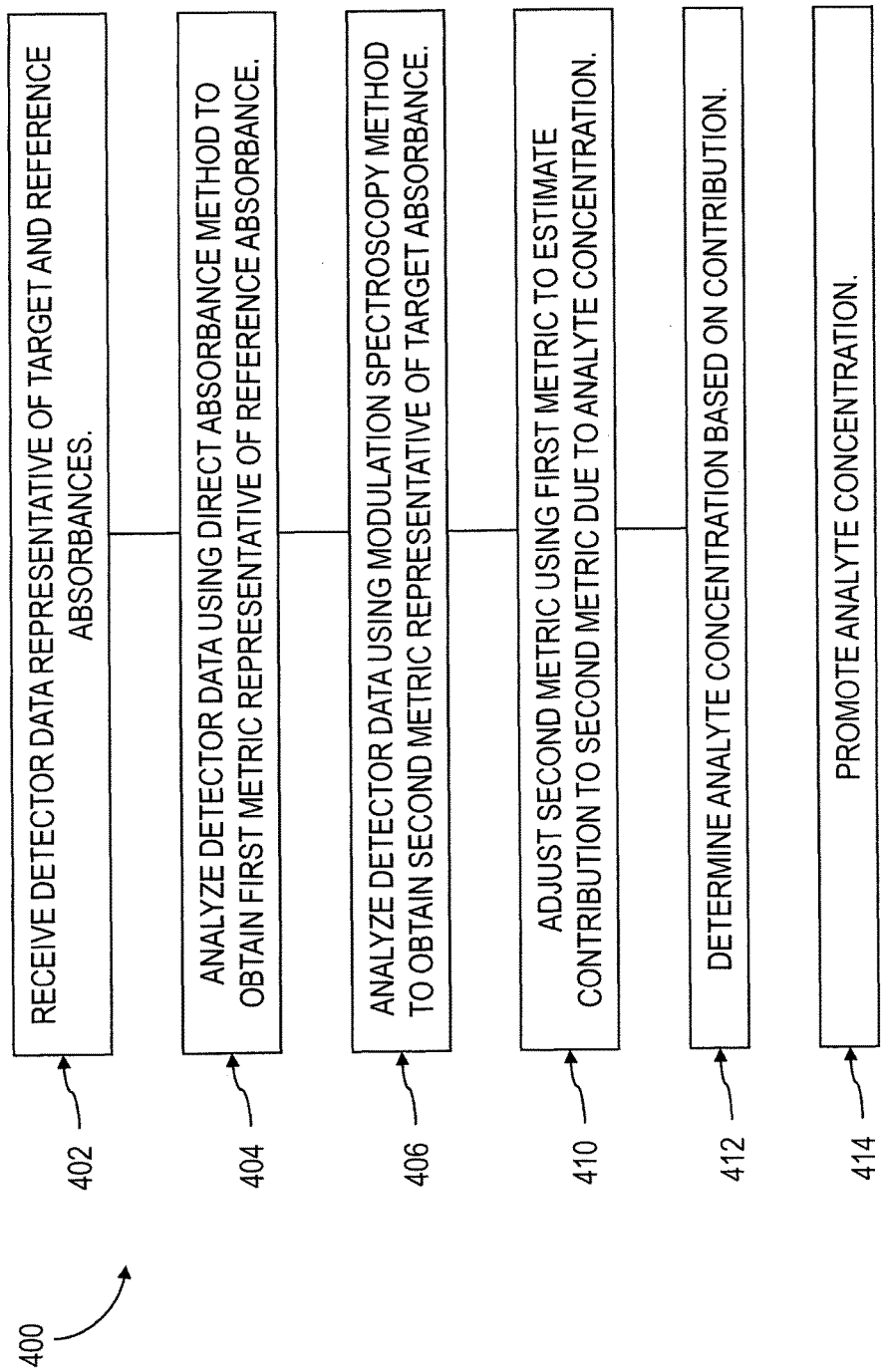
FIG. 4 is a process flow diagram illustrating a method.

An implementation of the above-described approach is illustrated in the process flow chart 400 of FIG. 4. At 402, detector data representative of absorbances of light emitted from a light source as the light passes through a volume of gas over a path length are received. The volume of gas includes an analyte at an analyte concentration and a background compound at a background compound concentration, and the absorbances include a target absorbance influenced by the analyte concentration and the background gas concentration and a reference absorbance influenced by the background gas concentration. At 404, the detector data are analyzed using a direct absorbance method to obtain a first metric representative of the reference absorbance. At 406, the detector data are analyzed using a modulation spectroscopy method to obtain a second metric representative of the target absorbance. The second metric is adjusted at 410 using the first metric to estimate a contribution to the second metric due to the analyte concentration. The analyte concentration is determined at 412 based on the contribution to the second metric due to the analyte concentration, and the analyte concentration is promoted at 414.

The subject matter described herein can be embodied in systems, apparatus, methods, and/or articles depending on the desired configuration. In particular, various implementations of the subject matter described herein can be realized in digital electronic circuitry, integrated circuitry, specially designed application specific integrated circuits (ASICs), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input.

The subject matter described herein can be implemented in a computing system that includes a back-end component, such as for example one or more data servers, or that includes a middleware component, such as for example one or more application servers, or that includes a front-end component, such as for example one or more client computers having a graphical user interface or a Web browser through which a user can interact with an implementation of the subject matter described herein, or any combination of such back-end, middleware, or front-end components. The components of the system can be interconnected by any form or medium of digital data communication, such as for example a communication network. Examples of communication networks include, but are not limited to, a local area network ("LAN"), a wide area network ("WAN"), and the Internet.

The computing system can include clients and servers. A client and server are generally, but not exclusively, remote from each other and typically interact through a communication network. The relationship of client and server arises by virtue of computer programs running on the respective computers and having a client-server relationship to each other.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow depicted in the accompanying figures and/or described herein do not necessarily require the particular order shown, or sequential order, to achieve desirable results. Other implementations may be within the scope of the following claims.

What is claimed:

1. A method comprising:
   controlling a light source to pass light through a volume of gas comprising an analyte at an analyte concentration, the controlling comprising adding a modulation frequency to the light;
   generating, using a detector, detector data representative of absorbance of the light as it passes through the volume of the gas between the light source and the detector;
   analyzing, using at least one processor, the detector data using a first analysis method to obtain a first calculation of the analyte concentration, the first analysis method having a first target range, the first analysis method comprising modulation spectroscopy;
   determining, using the at least one processor, that the first calculation of the analyte concentration indicates that the analyte concentration is outside of the first target range;
   controlling, in response to determining that the first calculation of the analyte concentration indicates that the analyte concentration is outside of the first target range, the light source to pass light without the modulation frequency through the volume of the gas;
   generating, using the detector, second detector data representative of the absorbance of the light as it passes through the volume of the gas;
   analyzing, using the at least one processor, the second detector data using a second analysis method to obtain a second calculation of the analyte concentration, the second analysis method having a second target range that differs from and extends outside of the first target range, the second analysis method comprising direct absorbance spectroscopy; and
   designating, using the at least one processor, the second calculation as the analyte concentration when it is determined that the first calculation of the analyte concentration indicates that the analyte concentration is outside of the first target range, or using the second calculation to calibrate the first analysis method when it is determined that the first calculation of the analyte concentration indicates that the analyte concentration is within the first target range and when the first target range and the second target range overlap.

2. A method as in claim 1, wherein the first target range comprises values of the analyte concentration between zero and a threshold analyte concentration.

3. A method as in claim 2, wherein the threshold analyte concentration is predetermined based on analysis of one or more calibration samples using the first analysis method.

4. A method as in claim 1, wherein the light source is a tunable laser source emitting light in a range of wavelengths.

5. A method as in claim 1, wherein the detector data comprises intensity data for the light emitted from the light source both with and without the modulation frequency.

6. A computer program product comprising a non-transitory machine-readable medium storing instructions that, when executed by at least one processor, cause the at least one processor to perform operations comprising:

controlling, with a controller, a light source to pass light to a detector through a volume of gas comprising an analyte at an analyte concentration, the controlling consistent with data collection for a first analysis method and a second analysis method, the first analysis method having a first target range, and the controlling comprising adding a modulation frequency to the light;

receiving, using at least one processor, detector data representative of an absorbance of light emitted from the light source as the light passes through the volume of the gas over a path length;

analyzing, using the at least one processor, the detector data using the first analysis method to obtain a first calculation of the analyte concentration;

determining, using the at least one processor, that the first calculation of the analyte concentration indicates that the analyte concentration is outside of the first target range;

controlling, in response to determining that the first calculation of the analyte concentration indicates that the analyte concentration is outside of the first target range, the light source to pass light without the modulation frequency through the volume of the gas;

receiving, using the detector, second detector data representative of the absorbance of the light as it passes through the volume of the gas;

analyzing, using the at least one processor, the second detector data using the second analysis method to obtain a second calculation of the analyte concentration, the second analysis method having a second target range that differs from and extends outside of the first target range, the second analysis method comprising direct absorption spectroscopy using a first absorbance transition for the analyte and the second analysis method comprising modulation spectroscopy using a second absorbance transition for the analyte, the first absorbance transition being stronger than the second absorbance transition; and designating, using the at least one processor, the second calculation as the analyte concentration when it is determined that the first calculation of the analyte concentration indicates that the analyte concentration is outside of the first target range, and using the second calculation to calibrate the first analysis method when it is determined that the first calculation of the analyte concentration indicates that the analyte concentration is within the first target range and when the first target range and the second target range overlap.

7. A computer program product as in claim 6, wherein the first analysis method comprises modulation spectroscopy using a first absorbance transition for the analyte and the second analysis method comprises modulation spectroscopy using a second absorbance transition for the analyte, the first absorbance transition being stronger than the second absorbance transition.

8. A system comprising:
a light source, the light source emitting light with a path length through a volume of gas, the volume of the gas comprising an analyte at an analyte concentration;
a detector, the detector quantifying an absorbance of the light as the light passes between the light source and the detector along the path length through the volume of the gas;
a controller configured to perform operations comprising:
controlling the light source to pass light through a volume of the gas comprising an analyte at an analyte concentration, the controlling consistent with data collection for a first analysis method and a second analysis method, the first analysis method having a first target range, and the controlling comprising adding a modulation frequency to the light;
receiving detector data representative of an absorbance of light emitted from the light source as the light passes through the volume of the gas over the path length;
analyzing the detector data using the first analysis method to obtain a first calculation of the analyte concentration;
determining that the first calculation of the analyte concentration indicates that the analyte concentration is outside of the first target range;
controlling, in response to determining that the first calculation of the analyte concentration indicates that the analyte concentration is outside of the first target range, the light source to pass light without the modulation frequency through the volume of the gas;
receiving second detector data representative of the absorbance of the light as it passes through the volume of the gas;
analyzing the second detector data using the second analysis method to obtain a second calculation of the analyte concentration, the second analysis method having a second target range that differs from and extends outside of the first target range, and the second analysis method comprising direct absorption spectroscopy; and
designating the second calculation as the analyte concentration when it is determined that the first calculation of the analyte concentration indicates that the analyte concentration is outside of the first target range, and using the second calculation to calibrate the first analysis method when it is determined that the first calculation of the analyte concentration indicates that the analyte concentration is within the first target range and when the first target range and the second target range overlap.

9. A system as in claim 8, the detector comprises one or more of a photodiode, a photodetector, and a photoacoustic detector.

10. A system as in claim 8, wherein the light source comprises one or more of a tunable diode laser (TDL), a quantum cascade laser (QCL), a horizontal cavity laser, a vertical cavity surface emitting semiconductor laser (VCSEL), and a device for nonlinear frequency generation of tunable light.

11. A system as in claim 8, wherein the first analysis method comprises modulation spectroscopy using a first absorbance transition for the analyte and the second analysis method comprises modulation spectroscopy using a second absorbance transition for the analyte, the first absorbance transition being stronger than the second absorbance transition.

12. A method comprising:
controlling a light source to pass light through a volume of gas comprising an analyte at an analyte concentration, the controlling comprising adding a modulation frequency to the light;

generating, using a detector, detector data representative of absorbance of the light as it passes through the volume of the gas between the light source and the detector;

analyzing, using at least one processor, the detector data using a first analysis method to obtain a first calculation of the analyte concentration, the first analysis method having a first target range, the first analysis method comprising modulation spectroscopy and the first target range comprising values of the analyte concentration between zero and a threshold analyte concentration;

determining, using the at least one processor, that the first calculation of the analyte concentration indicates that the analyte concentration is outside of the first target range;

controlling, in response to determining that the first calculation of the analyte concentration indicates that the analyte concentration is outside of the first target range, the light source to pass light without the modulation frequency through the volume of the gas;

generating, using the detector, second detector data representative of the absorbance of the light as it passes through the volume of the gas;

analyzing, using the at least one processor, the second detector data using a second analysis method to obtain a second calculation of the analyte concentration, the second analysis method having a second target range that differs from and extends outside of the first target range, the second analysis method comprising direct absorbance spectroscopy; and designating, using the at least one processor, the second calculation as the analyte concentration when it is determined that the first calculation of the analyte concentration indicates that the analyte concentration is outside of the first target range.

13. A method comprising:

controlling a light source to pass light through a volume of gas comprising an analyte at an analyte concentration, the controlling comprising adding a modulation frequency to the light;

generating, using a detector, detector data representative of absorbance of the light as it passes through the volume of the gas between the light source and the detector;

analyzing, using at least one processor, the detector data using a first analysis method to obtain a first calculation of the analyte concentration, the first analysis method having a first target range, the first analysis method comprising modulation spectroscopy, the first target range comprising values of the analyte concentration between zero and a threshold analyte concentration;

determining, using the at least one processor, that the first calculation of the analyte concentration indicates that the analyte concentration is outside of the first target range;

controlling, in response to determining that the first calculation of the analyte concentration indicates that the analyte concentration is outside of the first target range, the light source to pass light without the modulation frequency through the volume of the gas;

generating, using the detector, second detector data representative of the absorbance of the light as it passes through the volume of the gas;

analyzing, using the at least one processor, the second detector data using a second analysis method to obtain a second calculation of the analyte concentration, the second analysis method having a second target range that differs from and extends outside of the first target range, the second analysis method comprising direct absorbance spectroscopy; and designating, using the at least one processor, the second calculation as the analyte concentration when it is determined that the first calculation of the analyte concentration indicates that the analyte concentration is outside of the first target range, wherein the threshold analyte concentration is predetermined based on analysis of one or more calibration samples using the first analysis method.

14. A method comprising:

controlling a light source to pass light through a volume of gas comprising an analyte at an analyte concentration, the controlling comprising adding a modulation frequency to the light;

generating, using a detector, detector data representative of absorbance of the light as it passes through the volume of the gas between the light source and the detector;

analyzing, using at least one processor, the detector data using a first analysis method to obtain a first calculation of the analyte concentration, the first analysis method having a first target range, the first analysis method comprising modulation spectroscopy;

determining, using the at least one processor, that the first calculation of the analyte concentration indicates that the analyte concentration is outside of the first target range;

controlling, in response to determining that the first calculation of the analyte concentration indicates that the analyte concentration is outside of the first target range, the light source to pass light without the modulation frequency through the volume of the gas;

generating, using the detector, second detector data representative of the absorbance of the light as it passes through the volume of the gas;

analyzing, using the at least one processor, the second detector data using a second analysis method to obtain a second calculation of the analyte concentration, the second analysis method having a second target range that differs from and extends outside of the first target range, the second analysis method comprising direct absorbance spectroscopy; and designating, using the at least one processor, the second calculation as the analyte concentration when it is determined that the first calculation of the analyte concentration indicates that the analyte concentration is within the first target range when the first target range and the second target range overlap, wherein the light source is a tunable laser source emitting the light in a range of wavelengths.

15. A method comprising:

controlling a light source to pass light through a volume of gas comprising an analyte at an analyte concentration, the controlling comprising adding a modulation frequency to the light;

generating, using a detector, detector data representative of absorbance of the light as it passes through the volume of the gas between the light source and the detector;

analyzing, using at least one processor, the detector data using a first analysis method to obtain a first calculation of the analyte concentration, the first analysis method having a first target range;

determining, using the at least one processor, that the first calculation of the analyte concentration indicates that the analyte concentration is outside of the first target range;

controlling, in response to determining that the first calculation of the analyte concentration indicates that the analyte concentration is outside of the first target range, the light source to pass light without the modulation frequency through the volume of the gas;

generating, using the detector, second detector data representative of the absorbance of the light as it passes through the volume of the gas;

analyzing, using the at least one processor, the second detector data using a second analysis method to obtain a second calculation of the analyte concentration, the second analysis method having a second target range that differs from and extends outside of the first target range; and designating, using the at least one processor, the second calculation as the analyte concentration when it is determined that the first calculation of the analyte concentration indicates that the analyte concentration is outside of the first target range, the detector data comprising intensity data for the light emitted from the light source both with and without the modulation frequency.

16. A method comprising:

controlling a light source to pass light through a volume of gas comprising an analyte at an analyte concentration, the controlling comprising adding a modulation frequency to the light;

generating, using a detector, detector data representative of absorbance of the light as it passes through the volume of the gas between the light source and the detector;

analyzing, using at least one processor, the detector data using a first analysis method to obtain a first calculation of the analyte concentration, the first analysis method having a first target range;

determining, using the at least one processor, that the first calculation of the analyte concentration indicates that the analyte concentration is outside of the first target range;

controlling, in response to determining that the first calculation of the analyte concentration indicates that the analyte concentration is outside of the first target range, the light source to pass light without the modulation frequency through the volume of the gas;

generating, using the detector, second detector data representative of the absorbance of the light as it passes through the volume of the gas;

analyzing, using the at least one processor, the second detector data using a second analysis method to obtain a second calculation of the analyte concentration, the second analysis method having a second target range that differs from and extends outside of the first target range; and designating, using the at least one processor, the second calculation as the analyte concentration when it is determined that the first calculation of the analyte concentration indicates that the analyte concentration is outside of the first target range, the second analysis method comprising direct absorption spectroscopy using a first absorbance transition for the analyte and the second analysis method comprises modulation spectroscopy using a second absorbance transition for the analyte, the first absorbance transition being stronger than the second absorbance transition.

17. A method comprising:

controlling a light source to pass light through a volume of gas comprising an analyte at an analyte concentration, the controlling comprising adding a modulation frequency to the light;

generating, using a detector, detector data representative of absorbance of the light as it passes through the volume of the gas between the light source and the detector;

analyzing, using at least one processor, the detector data using a first analysis method to obtain a first calculation of the analyte concentration, the first analysis method having a first target range;

determining, using the at least one processor, that the first calculation of the analyte concentration indicates that the analyte concentration is outside of the first target range;

controlling, in response to determining that the first calculation of the analyte concentration indicates that the analyte concentration is outside of the first target range, the light source to pass light without the modulation frequency through the volume of the gas;

generating, using the detector, second detector data representative of the absorbance of the light as it passes through the volume of the gas;

analyzing, using the at least one processor, the second detector data using a second analysis method to obtain a second calculation of the analyte concentration, the second analysis method having a second target range that differs from and extends outside of the first target range; and designating, using the at least one processor, the second calculation as the analyte concentration when it is determined that the first calculation of the analyte concentration indicates that the analyte concentration is outside of the first target range, the second analysis method comprising direct absorption spectroscopy using a first absorbance transition for the analyte and the second analysis method comprising modulation spectroscopy using a second absorbance transition for the analyte, the first absorbance transition being stronger than the second absorbance transition and the first absorbance transition for the analyte and the second absorbance transition for the analyte are both within a scan range of a tunable laser.

18. A method comprising:

controlling a light source to pass light through a volume of gas comprising an analyte at an analyte concentration, the controlling comprising adding a modulation frequency to the light;

generating, using a detector, detector data representative of absorbance of the light as it passes through the volume of the gas between the light source and the detector;

analyzing, using at least one processor, the detector data using a first analysis method to obtain a first calculation of the analyte concentration, the first analysis method having a first target range;

determining, using the at least one processor, that the first calculation of the analyte concentration indicates that the analyte concentration is outside of the first target range;

controlling, in response to determining that the first calculation of the analyte concentration indicates that the analyte concentration is outside of the first target range, the light source to pass light without the modulation frequency through the volume of the gas;
generating, using the detector, second detector data representative of the absorbance of the light as it passes through the volume of the gas;
analyzing, using the at least one processor, the second detector data using a second analysis method to obtain a second calculation of the analyte concentration, the second analysis method having a second target range that differs from and extends outside of the first target range; and
designating the second calculation as the analyte concentration when it is determined that the first calculation of the analyte concentration indicates that the analyte concentration is outside of the first target range, the second analysis method comprising direct absorption spectroscopy using a first absorbance transition for the analyte and the second analysis method comprising modulation spectroscopy using a second absorbance transition for the analyte, the first absorbance transition being stronger than the second absorbance transition, and the light source comprising a first tunable laser with a first scan range that comprises the first absorbance transition for the analyte and a second tunable laser with a second scan range that comprises the second absorbance transition for the analyte.

19. A system comprising:
a light source, the light source emitting light with a path length through a volume of gas, the volume of the gas comprising an analyte at an analyte concentration;
a detector, the detector quantifying an absorbance of the light as the light passes between the light source and the detector along the path length through the volume of the gas;
a controller configured to perform operations comprising:
controlling the light source to pass light through a volume of the gas comprising an analyte at an analyte concentration, the controlling consistent with data collection for a first analysis method and a second analysis method, the first analysis method having a first target range, and the controlling comprising adding a modulation frequency to the light;
receiving detector data from the detector, the detector data being representative of an absorbance of the light emitted from the light source as the light passes through the volume of the gas;
analyzing the detector data using the first analysis method to obtain a first calculation of the analyte concentration;
determining that the first calculation of the analyte concentration indicates that the analyte concentration is outside of the first target range;
controlling, in response to determining that the first calculation of the analyte concentration indicates that the analyte concentration is outside of the first target range, the light source to pass light without the modulation frequency through the volume of the gas;
recieving second detector data representative of the absorbance of the light as it passes through the volume of the gas;
analyzing the second detector data using the second analysis method to obtain a second calculation of the analyte concentration, the second analysis method having a second target range that differs from and extends outside of the first target range;
designating the second calculation as the analyte concentration when it is determined that the first calculation of the analyte concentration indicates that the analyte concentration is outside of the first target range,
wherein when the analyte concentration in the volume of gas is in a calibration range in which the first target range and the second target range overlap, the method further comprises calibrating the first analysis method using the second calculation of the analyte concentration.

\* \* \* \* \*